US008748191B2

(12) United States Patent
Kraus et al.

(10) Patent No.: US 8,748,191 B2
(45) Date of Patent: Jun. 10, 2014

(54) STOP-FLOW ANALYTICAL SYSTEMS AND METHODS

(75) Inventors: Paul R. Kraus, Apple Valley, MN (US); William M. Christensen, Hibbing, MN (US)

(73) Assignee: Ecolab USA Inc., St. Paul, MN (US)

( * ) Notice: Subject to any disclaimer, the term of this patent is extended or adjusted under 35 U.S.C. 154(b) by 76 days.

(21) Appl. No.: 12/848,450

(22) Filed: Aug. 2, 2010

(65) Prior Publication Data

US 2012/0028364 A1  Feb. 2, 2012

(51) Int. Cl.
*G01N 21/78* (2006.01)
*G01N 21/05* (2006.01)
*G01N 21/27* (2006.01)
*G01N 33/00* (2006.01)
*G01N 1/10* (2006.01)

(52) U.S. Cl.
USPC ............... 436/135; 422/62; 422/63; 422/67; 422/82; 422/82.05; 422/82.08; 422/82.09; 422/501; 422/502; 422/503; 422/504; 422/505; 436/129; 436/164; 436/166; 436/171; 436/174; 436/179; 436/180

(58) Field of Classification Search
USPC .................. 422/62–63, 67, 81–82, 82.05, 422/82.08–82.09, 501–505; 436/129, 135, 436/164, 166, 171–172, 174, 179–180
See application file for complete search history.

(56) References Cited

U.S. PATENT DOCUMENTS

| 3,419,358 | A | * | 12/1968 | Smythe et al. .................. 436/54 |
| 3,527,570 | A | * | 9/1970 | Penhasi ............................ 422/81 |
| 3,554,226 | A | * | 1/1971 | Robbins et al. ............... 137/559 |
| 3,615,234 | A | * | 10/1971 | Ludvigsen ....................... 422/82 |
| 3,690,833 | A | * | 9/1972 | Ferrari .............................. 436/53 |
| 3,834,821 | A | * | 9/1974 | Ferrari et al. .................. 356/411 |
| 3,921,439 | A | * | 11/1975 | Burns ........................... 73/61.41 |
| 3,970,388 | A | * | 7/1976 | Hacker ............................ 356/72 |
| 3,981,487 | A | * | 9/1976 | Papoff et al. .................. 366/143 |
| 4,056,258 | A | * | 11/1977 | Papoff et al. ............... 366/160.4 |
| 4,090,129 | A | * | 5/1978 | Gear ............................. 324/71.1 |
| 4,199,419 | A | * | 4/1980 | Holroyd et al. ............ 204/157.5 |
| 4,224,033 | A | | 9/1980 | Hansen et al. |
| 4,333,356 | A | * | 6/1982 | Bartels et al. ............... 73/864.21 |
| 4,399,101 | A | * | 8/1983 | Queen ........................ 422/82.09 |
| 4,399,225 | A | * | 8/1983 | Hansen et al. .................. 436/34 |

(Continued)

FOREIGN PATENT DOCUMENTS

JP  60010175  1/1985

OTHER PUBLICATIONS

Dulz, G. et al, Inorganic Chemistry 1963, 2, 917-921.*
Becwith, P. M. et al, Analytical Chemistry 1972, 44, 221-227.*

(Continued)

*Primary Examiner* — Arlen Soderquist
(74) *Attorney, Agent, or Firm* — Fredrikson & Byron, P.A.

(57) ABSTRACT

Analytical systems and methods are provided for simultaneously dispensing metered volumes of fluids at different rates and mixing the fluids to generate a mixed sample having the fluids in proportion to the different rates at which they were dispensed. In some cases two or more of the fluids are premixed prior to mixing with other fluids. In some cases a use composition and diluent are simultaneously dispensed at different rates and premixed to form a diluted sample. One or more reagents may be mixed with the diluted sample and the sample mixture can be analyzed to determine characteristics of the use composition.

34 Claims, 7 Drawing Sheets

(56) References Cited

U.S. PATENT DOCUMENTS

| | | | | |
|---|---|---|---|---|
| 4,504,443 | A * | 3/1985 | Hansen et al. | 422/81 |
| 4,520,108 | A | 5/1985 | Yoshida et al. | |
| 4,680,271 | A * | 7/1987 | Williams | 436/55 |
| 4,702,393 | A * | 10/1987 | Chen | 222/1 |
| 4,794,806 | A * | 1/1989 | Nicoli et al. | 73/863.01 |
| 4,900,682 | A * | 2/1990 | Fischer et al. | 436/129 |
| 4,908,187 | A * | 3/1990 | Holmquist et al. | 422/81 |
| 4,910,151 | A * | 3/1990 | Platt | 436/163 |
| 4,911,891 | A * | 3/1990 | Platt | 422/68.1 |
| 4,920,056 | A * | 4/1990 | Dasgupta | 436/50 |
| 5,019,515 | A * | 5/1991 | Gisin et al. | 436/52 |
| 5,080,866 | A * | 1/1992 | Petty et al. | 422/80 |
| 5,081,045 | A * | 1/1992 | McGill | 436/55 |
| 5,084,381 | A * | 1/1992 | Akimoto et al. | 435/11 |
| 5,098,186 | A * | 3/1992 | Bull | 356/246 |
| 5,109,347 | A * | 4/1992 | Quick et al. | 700/240 |
| 5,139,956 | A * | 8/1992 | Schick et al. | 436/52 |
| 5,438,002 | A | 8/1995 | Mallard de la Varende et al. | |
| 5,447,692 | A * | 9/1995 | Keenan et al. | 422/116 |
| 5,474,938 | A * | 12/1995 | Jadesjo et al. | 436/25 |
| 5,503,720 | A * | 4/1996 | Teske | 205/787 |
| 5,547,875 | A * | 8/1996 | Petty et al. | 436/8 |
| 5,702,955 | A * | 12/1997 | Pugia | 436/135 |
| 5,928,953 | A * | 7/1999 | Kallback | 436/52 |
| 5,988,236 | A | 11/1999 | Fawcett | |
| 6,200,814 | B1 * | 3/2001 | Malmqvist et al. | 436/52 |
| 6,706,527 | B2 * | 3/2004 | Szecsody | 436/25 |
| 6,812,032 | B1 * | 11/2004 | Carver et al. | 436/63 |
| 6,855,296 | B1 | 2/2005 | Baker | |
| 6,885,883 | B2 * | 4/2005 | Parris et al. | 600/347 |
| 7,192,554 | B2 * | 3/2007 | Read | 422/28 |
| 7,220,383 | B2 * | 5/2007 | Anderson et al. | 422/62 |
| 7,349,760 | B2 | 3/2008 | Wei | |
| 7,361,157 | B2 | 4/2008 | Yamazaki | |
| 7,711,493 | B2 * | 5/2010 | Bartkowiak et al. | 702/19 |
| 8,071,390 | B2 * | 12/2011 | Tokhtuev et al. | 436/164 |
| 8,076,155 | B2 * | 12/2011 | Tokhtuev et al. | 436/164 |
| 8,143,070 | B2 * | 3/2012 | Tokhtuev et al. | 436/164 |
| 8,153,063 | B2 * | 4/2012 | Feldman et al. | 422/68.1 |
| 2003/0143746 | A1 * | 7/2003 | Sage, Jr. | 436/8 |
| 2003/0175983 | A1 * | 9/2003 | Wei et al. | 436/163 |
| 2003/0231294 | A1 | 12/2003 | Wariar | |
| 2004/0060818 | A1 * | 4/2004 | Feldman et al. | 204/403.01 |
| 2005/0208669 | A1 * | 9/2005 | Kaneko et al. | 436/72 |
| 2005/0272159 | A1 * | 12/2005 | Ismagilov et al. | 436/163 |
| 2006/0003461 | A1 * | 1/2006 | Chai et al. | 436/135 |
| 2006/0121622 | A1 * | 6/2006 | Crippen et al. | 436/135 |
| 2006/0188997 | A1 * | 8/2006 | Abramson et al. | 436/164 |
| 2008/0277615 | A1 * | 11/2008 | Gilbert et al. | 251/335.1 |
| 2008/0305553 | A1 | 12/2008 | Kraus | |
| 2009/0034359 | A1 * | 2/2009 | Cardonne et al. | 366/116 |
| 2009/0142846 | A1 * | 6/2009 | Crenshaw et al. | 436/34 |
| 2009/0145202 | A1 * | 6/2009 | Tokhtuev et al. | 73/61.48 |
| 2009/0145485 | A1 * | 6/2009 | Smith et al. | 137/2 |
| 2009/0147822 | A1 * | 6/2009 | Tokhtuev et al. | 374/142 |
| 2009/0150086 | A1 * | 6/2009 | Tokhtuev et al. | 702/23 |
| 2009/0150106 | A1 * | 6/2009 | Erickson et al. | 702/85 |
| 2010/0233026 | A1 * | 9/2010 | Ismagliov et al. | 422/68.1 |
| 2010/0304494 | A1 | 12/2010 | Tokhtuev et al. | |
| 2011/0070654 | A1 | 3/2011 | Tokhtuev et al. | |
| 2011/0165025 | A1 * | 7/2011 | Gransee et al. | 422/82.05 |
| 2012/0028364 | A1 * | 2/2012 | Kraus et al. | 436/127 |
| 2012/0149121 | A1 * | 6/2012 | Tokhtuev et al. | 436/129 |

OTHER PUBLICATIONS

Mieling, G. L. et al, Analytical Chemistry 1976, 48, 1686-1693.*
Pardue, H. L. et al, Clinical Chemistry 1977, 23, 1230-1237.*
Liebhafsky, H. A. et al, Journal of the American Chemical Society 1978, 100, 87-91.*
Stieg, S. et al, Analytical Chemistry 1980, 52, 796-800.*
Loriguillo, A. et al, Analytica Chimica Acta 1987, 199, 29-40.*
Perez-Bendito, D. et al, Journal of Pharmaceutical & Biomedical Analysis 1989, 7, 1435-1440.*
Jianhua, W. et al, Analytica Chimica Acta 1995, 303, 241-246.*
Zhang, K. et al, Talanta 2000, 51, 179-186.*
Paleologos, E. K. et al, Analytical Chemistry 2002, 74, 100-106.*
Awad, M. I. et al, Analytical Chemistry 2003, 75, 2688-2693.*
Messina, G. A. et al, Talanta 2004, 64, 1009-1017.*
Pettas, I. A. et al, Analytica Chimica Acta 2004, 522, 275-280.*
Hoag, C. M., Journal of Chemical Education 2005, 82, 1823, 1825.*
Iio, T et al, Biochemistry 1974, 13, 2915-2923.*
Davies, D. M. et al, Analyst 1988, 113, 1477-1479.*
White, H. D. et al, Biochemistry 1997, 36, 11828-11836.*
Saha, A. et al, Free Radical Biology & Medicine 1998, 24, 653-659.*
Buet, P. et al, Analytical Chemistry 2001, 73, 857-863.*
Furtmuller, P. G. et al, Biochemistry 2002, 41, 11895-11900.*
Muthusamy, M. et al, Journal of the American Chemical Society 2003, 125, 11150-11151.*
Olojo, R. et al, Journal of Physical Chemistry A 2004, 108, 1018-1023.*
Zhu, Z. et al, Macromolecules 2005, 9803-9812.*
Yeh, H.-C. et al, Biochemistry 2009, 48, 917-928.*
Pashkova, A. et al, Review of Sciencetific Instruments 2009, 80, 055104.*
Pinsent, B. R. W., Discussions of the Faraday Society 1954, 17, 140-141.*
Lymn, R. W. et al, Biochemistry 1970, 9, 2975-2983.*
Lymn, R. W. et al, Review of Scientific Instruments 1971, 42, 356-358.*
Fersht, A. R. et al, Biochemistry 1975, 14, 3350-3356.*
Morelli, B., Analytica Chimica Acta 1979, 106, 73-79.*
Krottinger, D. L. et al, Talanta 1979, 23, 549-561.*
Barman, T. E. et al, European Journal of Biochemistry 1980, 110, 397-403.*
Cash, D. J. et al, Analytical Biochemistry 1981, 112, 39-51.*
Karpen, J. W. et al, Analytical Biochemistry 1981, 135, 83-94.*
Langowski, J. et al, Analytical Biochemistry 1984, 142, 91-97.*
Scopes, R. K. et al, Analytical Biochemistry 1987, 165, 258-268.*
Goez, M., Journal of Physics E Scientific Instruments 1988, 21, 440-442.*
Sharma, V. S., Methods in Enzymology 1994, 232, 430-445.*
Gupta, D. et al, Dalton Transactions 2009, 5730-5736.*
Panine, P. et al, Advances in Colloid and Interface Science 2006, 127, 9-18.*
English Abstract, JP60010175, Parallel Stopped Flow Analyzer, Jan. 19, 1985, 1 page.
Awad et al., Potentiometric Analysis of Peroxyacetic Acid in the Presence of a Large Excess of Hydrogen Peroxide, Journal of Electroanalytical Chemistry, 544 (2003), 35-40.
FIAlab, Sequential Injection Lab-On-Valve Manifold, http://www.flowinjection.com/SIZ_Addons/SIA_LOV,aspx, downloaded Sep. 29, 2009, 1 page.
Bio-Logic, Stopped-Flow/Quench-Flow, http://www.bio-logic.info/rapid-kinetics/mixers,thml, downloaded Jun. 12, 2008, 13 pages.
Awad et al., Simultaneous Potentiometric Determination of Peracetic Acide and Hydrogen Peroxide, Anal. Chem., 2003, 75, 2688-2693.
Applied Photophysics, XS20 Stopped-Flow Spectrometer, http://www.photophysics.com/stoppedflow/index.php, downloaded Jun. 12, 2008, 2 pages.
KinTek Corporation, Stopped Flow and Quench Flow, http://www.kintek-corp.com, downloaded Jun. 12, 2008, 2 pages.
KinTek Corporation, Model SF-2004 Stopped-Flow, Copyright 2004, 8 pages.
KinTek Corporation, MiniMixer Stopped-Flow, Copyright 2004, 2 pages.
Horiba, Spex Stopped-Flow Accessory, Apr. 2006, 2 pages.
Hi-Tech Scientific Products, http://www.hi-techsci.com/spectro.html, downloaded Jun. 12, 2008, 3 pages.
Applied Photophysics, RX 2000 Rapid Mixing Stopped-Flow Accessory, http://www.photophysics.com/rx2000.php, downloaded Jun. 12, 2008, 2 pages.
Applied Photophysics, RX 2000 Rapid Kinetics Spectrometer Accessory, Feb. 2006, 2 pages.
New Era Pump Systems, Inc., NE-1600/1800 Multi-Syringe Pump, http://syringepump.com/NE-16001800.htm, downloaded Jun. 7, 2010, 3 pages.

(56) References Cited

OTHER PUBLICATIONS

Haydon, 43000 Series Size 17 Stepper Motor Linear Actuators, http://www.haydonkerk.com/Linerar/ActuatorProducts/StepperMotorLinearActuatorsHybrid/size17LinearActuator/tabid/79/Default.aspx, downloaded Jun. 7, 2010, 7 pages.

Pinkernell, et al., Simultaneous HPLC Determination of Peroxyacetic Acid and Hydrogen Peroxide, Analytical Chemistry, vol. 69, No. 17, Sep. 1, 1997, 6 pages.

Awad, et al., Kinetic Studies on the Oxidation of Iodide by Peroxyacetic Acid, Inorganica Chimica Acta 344 (2003), 253-256.

Alcocer, et al., A Microcomputer-Based High-Speed Data-Acquisition System for a Stopped-Flow Spectrophotometer: PDP-11 Architecture Interfaced to a Commercial Instrument, Journal of Automatic Chemistry, vol. 5, No. 2 (Apr.-Jun. 1983, 6 pages.

Pinkernell, et al., Selective Photometric Determination of Peroxycarboxylic Acids in the Presence of Hydrogen Peroxide, Analyst, Jun. 1997, vol. 122, 5 pages.

* cited by examiner

STOP-FLOW ANALYTICAL SYSTEMS AND METHODS

FIELD

This disclosure generally relates to analytical systems and methods for performing wet chemical analysis. In particular, this disclosure relates to stop-flow analytical systems and methods for determining characteristics of one or more substances within a use composition.

BACKGROUND

Wet chemical analyses often include a series of operations that ultimately produce a desired measurement or characterization. One step often involves the delivery of predetermined volumes of one or more fluid chemicals into a mixing chamber. In some cases known ratios of chemicals are mixed and the resulting mixture is then analyzed to determine one or more properties of the mixture and/or its constituents. Some analyses may also characterize the mixture and/or its constituent parts based on one or more reactions occurring in the mixture.

When performed by hand, chemical analyses can produce varied results due to a number of factors such as, for example, the usage of an improper or inaccurate volume of a fluid chemical. Moreover, manual analytical chemistry procedures can be tedious and time consuming. Current attempts at automating steps in a chemical analysis provide some benefits over manual procedures, but drawbacks persist. For example, circumstances may require an increased sampling frequency that current manual and automated analysis methods and systems cannot accommodate with required accuracy and precision. Often large volumes of chemicals and/or fluid samples are also needed for analysis with current systems and methods, leading to expensive and wasteful operation.

One application of analytical chemistry is to determine the concentration of one or more analytes within a composition. For example, analytical chemical procedures can be useful in the analysis and monitoring of antimicrobial compositions. Antimicrobial compositions are used in a variety of automated processing and cleaning applications to reduce microbial or viral populations on hard or soft surfaces or in a body or stream of water. For example, antimicrobial compositions are used in various applications including kitchens, bathrooms, factories, hospitals and dental offices. Antimicrobial compositions are also useful in the cleaning or sanitizing of containers, processing facilities or equipment in the food service or food processing industries, such as cold or hot aseptic packaging. Antimicrobial compositions are also used in many other applications including but not limited to clean-in-place systems (CIP), clean-out-of-place systems (COP), washer-decontaminators, sterilizers, textile laundry machines, filtration systems, etc.

Whatever the application, an antimicrobial or "use" composition is a composition containing a defined minimum concentration of one or more active components which exhibit desired antimicrobial properties. One such category of active antimicrobial components include peracids, such as peroxycarboxylic acid (peracid), peroxyacid, peroxyacetic acid, peracetic acid, peroctanoic acid, peroxyoctanoic acid and others.

The concentration of active components in the use composition is chosen to achieve the requisite level of antimicrobial activity. In use compositions in which one or more peracids are the active component, and in the instance of a recirculating process, the concentration of hydrogen peroxide tends to increase over time while the concentration of peracid decreases. However, in order to maintain the requisite level of antimicrobial activity, the amount of peracid in the use composition must be maintained at a defined minimum concentration. In addition, as the amount of hydrogen peroxide in the use composition increases, the use composition may exceed a defined maximum concentration of hydrogen peroxide in the solution. In some applications, for example bottling line cleansing, the allowable amount of residual hydrogen peroxide is subject to government regulations. Once the hydrogen peroxide concentration exceeds the maximum concentration, the spent use composition is discarded and a new use composition generated.

To ensure that the amount of peracid is maintained at or above some minimum concentration and to determine when the amount of hydrogen peroxide reaches or exceeds a maximum concentration, it is necessary to determine the concentration of peracid(s) and hydrogen peroxide in the use composition. In the past, to determine properties such as the peracid concentration and the hydrogen peroxide concentration in a use composition has required multiple time consuming manual titrations, several different reagents and relatively large volumes of use composition. Also, past automated systems designed to address one or more of these undesirable traits have also exhibited less than desired sampling frequency and difficulties with online deployment in the field.

SUMMARY

Embodiments of the invention are generally directed to designs for an analytical system and/or method capable of delivering and mixing volumes of fluid chemicals, such as use compositions and reagents, and then testing the resulting mixture to determine one or more properties of the mixture and/or its constituent parts.

According to one aspect of the invention, an analytical system is provided including a sample pump, a first reagent pump, and a diluent pump. Each of the sample, first reagent, and diluent pumps is coupled with an input port that allows the pump to be coupled with a fluid source, i.e., a working source of a use composition, a source of a first reagent, and a source of a diluent, respectively. The system includes a pre-mixer coupled to the sample pump and the diluent pump that is configured to mix together a sample of the use composition delivered by the sample pump and a volume of the diluent delivered by the diluent pump, resulting in a diluted sample. A mixer is coupled to the first reagent pump and the pre-mixer, and configured to mix together a volume of the first reagent delivered by the first reagent pump and the diluted sample received from the pre-mixer to create a sample mixture. The system also includes an optical sensor coupled to the mixer for testing the sample mixture. In some embodiments the optical sensor includes an optical cell that receives the sample mixture from the mixer. The optical sensor is configured to obtain response data from the sample mixture indicative of one or more properties of one or more substances within the use composition. In some embodiments the optical sensor is configured to obtain response data indicative of the concentrations of the one or more substances within the use composition.

According to another aspect of the invention, an analytical system is provided that includes sample pumping means coupled with a sample input port that allows the sample pumping means to be coupled to a working source of a use composition having concentrations of one or more substances. The system also includes first and second reagent pumping means coupled with first and second reagent input ports, respectively, that allow the first and second reagent pumping means to be coupled with a source of a first reagent and a source of a second reagent, respectively. The system also includes diluent pumping means coupled with a diluent input port that allows the diluent pumping means to be coupled with a source of a diluent. A pre-mixing means is provided and coupled to the sample pumping means and the diluent pumping means for mixing together a sample of the use composition delivered by the sample pumping means and a volume of the diluent delivered by the diluent pumping means. The premixing results in a diluted sample. Mixing means are coupled to the first reagent pumping means, the second reagent pumping means, and the pre-mixing means, for mixing together a volume of the first reagent delivered by the first reagent pumping means, a volume of the second reagent delivered by the second reagent pumping means, and the diluted sample received from the pre-mixing means, resulting in a sample mixture. The system also includes optical sensing means coupled to the mixing means for receiving the sample mixture from the mixing means and obtaining response data from the sample mixture indicative of the concentrations of the one or more substances within the use composition.

According to another aspect of the invention, a method for determining concentrations of a peracid and/or a peroxide within a use composition is provided. The method includes receiving use composition with a sample pump, the use composition having concentrations of a peracid and/or a peroxide from a working source of the use composition. The method also includes receiving a first reagent and second reagent with a first reagent pump and a second reagent pump, respectively, and receiving a diluent with a diluent pump. The method also includes simultaneously actuating the sample pump, the first reagent pump, the second reagent pump, and the diluent pump to dispense a sample of the use composition, a volume of the first reagent, a volume of the second reagent, and a volume of the diluent. The sample of the use composition is premixed with the volume of the diluent to form a diluted sample. The volumes of the first reagent and the second reagent are mixed with the diluted sample to form a mixed sample. The method also includes obtaining optical response data from the mixed sample indicative of the concentrations of the peracid and/or the peroxide and determining the concentrations of the peracid and/or peroxide based on the optical response data.

Embodiments of the present invention can provide one or more of the following features and/or advantages. Some embodiments provide an analytical system including two or more fluid dispensing lines capable of being coupled with sources of fluids, enabling parallel dispensing of the fluids into a mixer. The analytical system can in some cases simultaneously dispense one or more reagents and a sample of a use composition into a mixer, enabling rapid dispensing and mixing of the fluids prior to analysis with a sensor. Some embodiments of the invention provide an analytical system including an actuator or drive mechanism capable of driving two or more fluid pumps at different rates, allowing dispensing and mixing of the fluids in a desired proportion. In some cases the actuator includes independent drive mechanisms that dispense reagents, use composition, and/or diluent at two or more different rates. In some cases the system includes an asynchronous actuator with a single drive mechanism that drives two or more pump syringes at different rates.

Some embodiments provide an analytical system that can be integrated with an online use composition system to monitor properties of the use composition in real time or near real time. The analytical system may be coupled with the use composition system in the field, allowing it to receive a sample of the use composition for on-site and/or online analysis. In some cases the analytical system premixes the sample of use composition with a diluent prior to analysis. This enables direct sampling and accurate online analysis of a use composition having relatively high concentrations of an active component. In some cases a sample of a use composition, a diluent, and one or more reagents are simultaneously dispensed into a mixer, with the sample and diluent being premixed enroute to the mixer. Such a system provides desired concentrations of active components within the sample to ensure a desired reaction with the one or more reagents within the mixer. Such a system can also adjust the concentrations of the active components within the sample to be compatible with the operating range of a sensor coupled with the mixer.

These and various other features and advantages will be apparent from a reading of the following detailed description.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION OF THE PREFERRED EMBODIMENTS

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
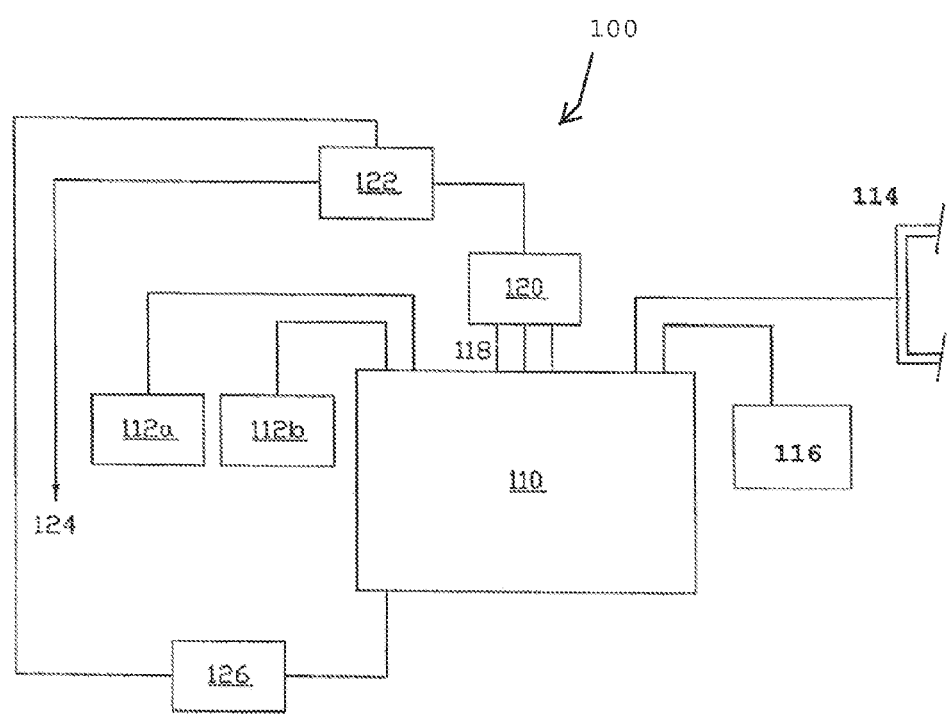
FIG. 1 is a schematic diagram of an analytical system coupled with a use composition system according to some embodiments of the invention.

FIG. 1 shows a schematic view of an analytical system 100 according to some embodiments of the invention. The analytical system 100 includes a sample preparation and dispensing assembly 110 in fluid connection with multiple sources of fluid 112, 114, 116. The fluid sources can generally include any suitable reservoir or other container for holding a desired fluid (e.g., a portable or on-site container) or in some cases may include a plumbed fluid line incorporated into a larger fluid network (e.g., a water pipe network, a use composition system). The sample preparation assembly 110 manages the simultaneous dispensing of predetermined volumes of selected ones of the connected fluids. The metered fluids are dispensed via fluid dispensing lines 118 connected with the sample preparation assembly 110. A mixer 120 connected with the fluid dispensing lines 118 mixes the dispensed fluids, creating a sample mixture. The sample mixture is delivered to a sensor 122, which can obtain response data indicative of characteristics of the sample mixture. Once the fluid has passed through sensor 122, it can be disposed of via connection to a waste outlet 124. Operation of the sample preparation assembly 110 and sensor 122 can be controlled by a controller 126. In addition, the controller 126 may be coupled with the sensor 122 in order to process the response data to determine properties of the sample mixture or one or more of the fluids within the mixture.

According to some embodiments, analytical systems such as the analytical system 100 depicted in FIG. 1 enable the automation of wet chemical analytical procedures. As just one example, the analytical system 100 can be configured as a use composition analyzer. A use composition analyzer may be connected to a source of use composition 114 to analyze characteristics of the use composition such as, for example, the presence or concentration of selected analytes within the use composition. In some cases the system 100 mixes the use composition with one or more reagents from the fluid sources 112*a*, 112*b* and measures properties of the mixture in order to determine characteristics of the use composition. In some embodiments the source of use composition 114 is a "working" source, such that the analytical system 100 can directly sample the use composition as it actively circulates through a working system. In such cases the analytical system 100 is simultaneously online with the use composition system at the same site, allowing monitoring of certain characteristics of the use composition in real time or near real time.

In particular, some embodiments are well suited for use as a use composition monitor for determining the concentration of peracid and/or hydrogen peroxide (occasionally referred to herein simply as "peroxide" or $H_2O_2$) in a use composition, as will be discussed further herein. For example, the use composition may be monitored to ensure that the concentration of peracid satisfies at least a minimum threshold concentration. The use composition may also be monitored to determine when the concentration of peroxide exceeds a maximum threshold concentration. Of course, while embodiments of the analytical systems are disclosed herein related to the monitoring of a use composition, the invention is not to be limited to monitoring devices, the monitoring of a "use composition", or the specific use compositions disclosed herein. For example, embodiments of the invention can be used as off-line and/or remote (e.g., laboratory) analytical instruments or for other purposes. In addition, an analytical system can be adapted to analyze any number of fluid chemicals. Accordingly, embodiments of the invention encompass and enable the automation of wet chemical analytical procedures in which metered volumes of two or more fluids are mixed and subsequently measured to determine one or more properties of the fluids.

Returning to FIG. 1, in some cases the analytical system 100 is controlled by the controller 126. The controller 126 may include a computer processor and/or other computing hardware programmed with software instructions for carrying out the analysis and/or monitoring of the use composition. In certain embodiments, the controller is coupled with the sample preparation/dispensing assembly 110 and controls the assembly 110 to receive and dispense predetermined volumes of fluids into the mixer 120. The sample preparation assembly 110 provides for the synchronous delivery of a plurality of fluids to the mixer 120 and sensor 122. Thus, a sample can be prepared by parallel processing of multiple fluids, rather than the serial preparation of sample mixtures characteristic of sequential injection analysis systems. Parallel processing of sample mixtures can afford significant reductions in sample preparation time, thus decreasing the time required to perform a measurement cycle. Accordingly, embodiments according to the present invention can provide for more frequent use composition analysis than in past designs.

In addition, some embodiments of the analytical system 100 allow for dilution of one or more fluids prior to mixing within the mixer 120. In FIG. 1 for example, the sample preparation/dispensing assembly 110 is fluidly connected to a source 116 of diluent, such as water. The system 100 can use the diluent received from the diluent source 116 to dilute the use composition received from the working use composition source 114. Such dilution can be useful when the use composition has one or more substances in a concentration outside the normal operating range of the analytical system's instrumentation. Accordingly, the system 100 can receive and analyze the use composition by diluting the use composition when necessary so that the diluted concentrations of the substances are compatible with its instrumentation, such as the sensor 122. The analytical system 100 advantageously conducts this dilution online, allowing the system 100 to analyze the use composition in real time or near real time despite potentially incompatible concentrations of substances within the use composition. Also, in some cases a use composition may be mixed with one, two, or more reagents depending upon the particular chemistry being employed. For example, as shown in FIG. 1, the use composition can be mixed with two reagents from sources 112*a*, 112*b*. Diluting the use composition can in some cases lower the concentrations of substances within the use composition, thus requiring smaller amounts of reagents from sources for mixing and reacting with the use composition.

Returning to FIG. 1, in some embodiments fluid inlet connectors, outlet connectors, and/or connections between the sample preparation assembly, the mixer 120, the sensor 122, and the fluid sources can comprise generally any fluid-tight connection, such as tubing. For example, connecting tubes can comprise standard 1 mm diameter tubing connected to the sample preparation assembly via threaded ferrule connection. Suitable tubing and connectors are available, for example, from Valco Instruments Co. Inc., of Houston, Tex.

The mixer 120 is coupled with the sample preparation assembly 110 via fluid dispensing lines 118. Any number of dispensing lines 118 may be provided, depending for example, upon the number of fluids being mixed and/or any pre-mixing within the sample preparation assembly 110. The dispensing lines 118 advantageously provide for simultaneous delivery of multiple fluids to the mixer 120. Upon reaching the mixer 120, the fluids from each of the dispensing lines are mixed, resulting in a sample mixture.

The mixer 120 can provide thorough mixing of metered fluid volumes dispensed by the sample preparation/dispensing assembly 110. In a use composition monitor, appropriate mixing can ensure that the response data measured by the sensor 122 leads to an accurate determination of the characteristic of the use composition to be determined. The mixer

120 may be implemented using any conventional device designed to rapidly mix together two or more fluids. For example, in some cases the mixer 120 may be a static mixer, such as a piece of tubing with internal baffles that cause flow reversal of the fluids to result in rapid mixing. The mixer 120 may also be implemented using a knotted reactor, reaction coil, an open tubular reactor, serpentine or other fluid mixing device known in the art. In some cases the mixer 120 may be a laminar flow mixer. An example baffle-type static mixer is the Series 120 Individual Mixing Elements available from TAH Industries Inc, Robbinsville, N.J. In some embodiments, the mixer 120 may take the form of a dynamic mixer such as a jet flow mixer. However, it shall be understood that any suitable mixer may be used without departing from the scope of the present invention, and that the invention is not limited in this respect.

The mixed sample of fluids (e.g., use composition and one or more reagents) is then delivered to the sensor 122. The sensor measures at least one characteristic of the sample mixture indicative of the properties to be determined. The measurements obtained by sensor 122 are referred to herein as "response data." For example, properties to be determined can be the concentrations of one or more substances (e.g., peracid and/or hydrogen peroxide) in the use composition. The controller 126 receives the response data from the sensor 122 and determines the properties based on the response data.

In some embodiments, the sensor 122 includes an optical cell that receives the sample mixture and an optical detector that measures the transmittance and/or the absorbance of the sample mixture while it is within the cell. In such embodiments, the response data may be optical transmittance data or optical absorbance data of the sample as a function of time. In certain embodiments, the sensor 122 may measure other characteristics indicative of the particular property to be determined, such as fluorescence, pH, oxidation-reduction potential, conductivity, mass spectra and/or combinations thereof. In such embodiments, the response data would be the corresponding measured characteristic at the appropriate points in time.

Examples of potentially useful sensors include photometric, pH, ORP, conductivity or other sensors. Photometric sensors can operate in the visible, ultraviolet or infrared wavelength range, although other luminescence detection techniques may also be used without departing from the scope of the present invention. One example of a suitable commercially available photometric detector can be assembled using a DT-MINI-2 Deuterium Tungsten Source, FIA-Z-SMA-PEEK Flow Cell and USB4000 Miniature Fiber Optic Spectrometer, all available from Ocean Optics Inc., Dunedin, Fla. It shall be understood, however, that any suitable optical detector may be used without departing from the scope of the present invention, and that the invention is not limited in this respect. Indeed, an appropriate optical sensor may be any of those described for use with respect to U.S. patent application Ser. No. 12/370,369, which is presently co-owned and is herein incorporated by reference.

Upon receiving the response data from the sensor 122 and determining the desired properties/characteristics of the sample mixture, the controller 126 may store and/or display the determined properties and/or initiate one or more further actions based upon the determined properties. For example, in some embodiments the controller 126 may initiate procedures to modify or replace a use composition based on the determined concentrations of one or more substances within the use composition. The controller 126 could initiate and control such processes, or instruct another component (e.g., a separate use composition controller not shown in FIG. 1) to modify or replace the use composition based on, e.g., the determined concentrations of the one or more substances. Accordingly, embodiments of the invention provide a real time or near real time feedback loop that provides analysis of a use composition from a working system and modifications to the use composition based on the analysis.

In some embodiments, the analytical system 100 can be adapted to perform a kinetic assay procedure for determining the concentrations of peracid and/or hydrogen peroxide in a use composition. This is accomplished by exploiting the difference in reaction rates between peracid and hydrogen peroxide when using, for example, a buffered iodide reagent to differentiate peracid and hydrogen peroxide concentrations when both these analyte compounds are present in the use composition. In such use the inputs of the sample preparation assembly 110 can be coupled with a source 112a of reagent, a source 112b of an acid or an acidic buffer, and a source 114 of the use composition. In addition, some embodiments can include a connection to a source 116 of diluent, such as water. In certain embodiments, such as with a multiple reagent system, the reagents may include a degassed iodide solution, such as potassium iodide, with a pH adjusted to the alkaline range and a dilute acid such as acetic acid to adjust the pH of the reacting species to a pH less than approximately 6.5. However, it shall be understood that other suitable reagents may also be used without departing from the scope of the present invention, and that the invention is not limited in this respect. The analytical system 100 may also determine the concentrations of peracid and/or peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

In a use composition including hydrogen peroxide and a peracid such as peroxyacetic acid, a buffered iodide changes color as it is oxidized by both the peroxyacetic acid and the hydrogen peroxide to form triiodide ion. However, as the peroxyacetic acid and the hydrogen peroxide in the use composition compete for the available iodide ions, reaction with the peroxyacetic acid proceeds at a faster rate than the reaction with the hydrogen peroxide, as shown in the following equations:

$$2CH_3COOOH + (excess)I^- \rightarrow I_3^- + 2CH_3COOH \quad \text{FASTER}$$

$$H_2O_2 + (excess)I^- + 2H^+ \rightarrow I_3^- + 2H_2O \quad \text{SLOWER}$$

This difference in reaction rates may be exploited to differentiate peracid and hydrogen peroxide concentrations when both these analyte compounds are present in the use composition. For example, the optical sensor 122 can measure colorimetric data as a function of time of a sample within the sensor 122. This data can include, for example, absorbance data of a sample mixture undergoing the above reactions. Because the triiodide product of the above reactions manifests as a change in absorbance, the measured colorimetric data can be used to determine the concentrations of peracid and peroxide within the use composition. In particular, the initial absorbance, $A_0$, is dependent on the peracid concentration and independent of the peroxide concentration; and the rate of change in absorbance, $A_r$, is dependent on the concentration of peroxide and independent of the peracid concentration. Accordingly, measurements of the initial absorbance $A_0$ and the rate of change of absorbance $A_r$ can be utilized to determine values of peracid and peroxide concentration within a use composition. This "peracid/peroxide chemical analysis" is described in more detail in commonly owned U.S. patent application Ser. Nos. 11/810,417 and 12/370,369, the contents both of which are hereby incorporated by reference in their respective entireties.

As used herein, the term "peracid" refers to any acid that in which the hydroxyl group (—OH) is replaced with the peroxy group (—OOH). The peracid(s) may be C2-C18 peracid(s), such as C2 (peracetic) acid and C8 (peroctanoic) acid. It shall be understood that the apparatus and/or methods of the present invention may detect the combined presence of all peracids in a sample, whether the sample contains one or more than one different peracids, and that the invention is not limited in this respect.

Peroxycarboxylic acids generally have the formula $R(CO_3H)_n$. In some embodiments, the R may be an alkyl, arylalkyl, cycloalkyl, aromatic or heterocyclic group, and n may be one or two.

Peroxycarboxylic acids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof as well others known to those of skill in the art.

Figure 2:
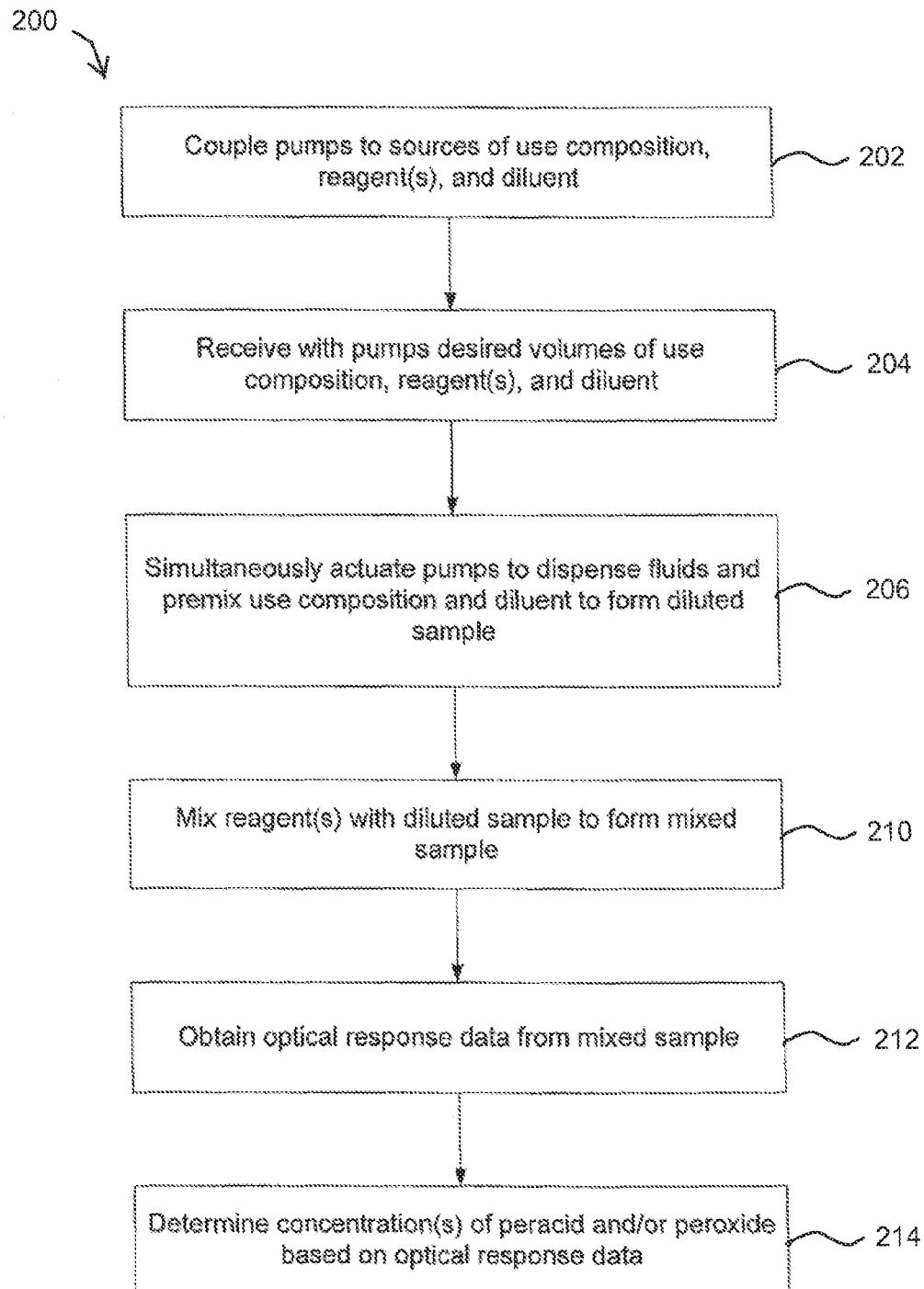
FIG. 2 is a flow diagram illustrating a method of determining chemical concentrations within a use composition according to some embodiments of the invention.

FIG. 2 is a flow diagram illustrating a method 200 for determining the concentration of peracid and/or hydrogen peroxide in a use composition according to some embodiments of the invention. The sequence of preparation and measurement steps can be carried out using any suitable analytical and/or monitoring instrument. In some cases the method can be carried out by the analytical system 100 depicted in FIG. 1. In this case the controller 126 may be programmed with instructions for causing the sample preparation/dispensing assembly 110 to receive and dispense one or more fluids into the mixer 120 and sensor 122, and then determine the concentrations of peracid and/or peroxide based on response data received from the sensor 122. In certain embodiments, the controller 126 may be programmed to determine the concentrations of peracid and/or peroxide on a periodic basis. The frequency at which the analytical system 100 determines the concentration of peracid and peroxide in the use composition is referred to herein as the "monitoring frequency" and may provide for analyzing the use composition every 1 minute, every 15 minutes, every 30 minutes, every hour, every two hours, every day or other appropriate time. The monitoring frequency/interval may vary depending on, among other things, the particular application to which the use composition is directed and the corresponding threshold concentrations of peracid and peroxide.

As will be discussed further herein, pumps are often coupled with sources of fluid to receive the fluid(s) and then dispense them in metered volumes. For example, an analytical system such as the system 100 of FIG. 1 will often include one or more pumps that receive fluids and then dispense them in metered volumes. As an initial or preliminary step, the method 200 includes coupling 202 a number of pumps to a source of a use composition, one or more sources of reagent(s), and a source of a diluent. For example, a portable analytical system (or even a permanent system upon first installation) is initially coupled to the appropriate fluid sources to provide the system with the necessary fluids for analysis of a use composition. The fluid sources can be standalone reservoirs or containers holding the appropriate fluids, or connections to a fluid delivery network such as water piping or a working use composition system. In the case of a system performing the peracid/peroxide chemical analysis described earlier herein, system pumps are coupled to a source of use composition, a source of a first reagent (e.g., an iodide solution), a source of a second reagent (e.g., an acid or acidic buffer), and a source of diluent.

After coupling 202 the pumps to the desired fluid sources, a measurement sequence can begin to determine the concentrations of peracid and/or peroxide in the use composition. At the start of each measurement sequence, the pumps receive 204 an amount of the use composition, an amount of one or more reagents, and an amount of diluent from the fluid sources. For example, with respect to the system 100 in FIG. 1, the controller 126 may actuate pumps within the sample preparation and dispensing assembly 110 to simultaneously draw in and receive a first reagent from source 112a, a second reagent from source 112b, a diluent from source 116, and the use composition from source 114. The manner in which the pumps draw and receive 204 the fluids can vary depending upon the type of pump (e.g., micropump, syringe pump, etc.) being utilized.

Turning back to FIG. 2, the method 200 includes simultaneously actuating 206 the system pumps to dispense metered volumes of the use composition, the reagent(s), and the diluent, and in some cases to optionally premix two or more of the fluids as will be described further herein. Simultaneously dispensing 206 the fluids advantageously allows for parallel processing of the fluids, rather than the serial preparation of sample mixtures characteristic of sequential injection analysis systems. Accordingly, the simultaneous dispensing 206 can afford significant reductions in sample preparation time, thus decreasing the time required to perform a measurement cycle. Thus embodiments according to the present invention can provide for more frequent use composition analysis.

In certain embodiments of the invention, the method 200 also includes simultaneously dispensing at least two fluids toward the mixer at different rates. Thus, fluids enter the mixer at different rates, allowing for preparation of a sample mixture having a desired proportion or ratio of the fluids. As just one example, in one case the use composition may be dispensed at a rate ten times slower than the dispensing rate of one of the reagents, thus causing the mixed sample to contain ten times more reagent than use composition assuming similar dispensing durations. The fluids can be dispensed at different rates using a variety of methods, including actuating independent pumps within the system at different rates. As will be discussed further herein, in some cases multiple pumps are actuated at different rates with a single driving mechanism.

In some embodiments the method 200 also includes the step of premixing 206 the use composition and the diluent to form a diluted sample prior to mixing with the one or more reagents. As discussed above, such dilution can be useful when the use composition has one or more substances in a concentration outside the normal operating range of the analytical system's instrumentation. For example, in some cases such as aseptic bottle washing, a use composition may have concentrations of peracid at about 2,000 ppm, which can exceed the absorbance capability of some optical sensors. Premixing the diluent and the use composition to form a diluted sample also allows for an effective reaction using a smaller amount of reagent than what otherwise might be necessary. For example, the peracid/peroxide chemistry discussed above requires a tenfold excess of potassium iodide relative to the amount of peracid and peroxide in the sample. By diluting the use composition, a smaller amount of potassium iodide can still yield an effective reaction.

In certain embodiments the step of premixing the use composition and diluent takes place as the use composition, diluent, and reagents are simultaneously dispensed 206, before the fluids are mixed 210 to form a sample mixture. Accordingly, the mixing portion of a measurement cycle can be shortened in some instances because all fluids can be simultaneously dispensed and the use composition and diluent can be premixed as they are dispensed, prior to mixing with the reagents, rather than requiring additional time for diluting the use composition prior to simultaneously dispensing the fluids. Thus, the method 200 provides an efficient dilution and mixing process that can be used for online dilution of the use composition. For example, the use composition can be sampled directly from the working use composition system, and then diluted, mixed with one or more reagents, and analyzed to determine properties of the use composition in real time or near real time despite potentially incompatible concentrations of substances within the use composition.

In many cases the ratio of diluent and use composition can be preset to correspond to an expected range of concentrations within a selected use composition. In certain embodiments, online predilution may also provide advantages for easily adapting an analytical system for analyzing multiple use compositions having varying concentrations of substances. For example, in some embodiments an analytical system is provided in a portable form, and may be used to analyze use compositions in a number of locations, wherein the use composition in each location may have a different range of concentrations of particular substances. In addition, in certain embodiments, an analytical system could be provided in a central location and be selectively connected to multiple use composition systems, allowing the single analytical system to monitor the concentrations within multiple use compositions. In such cases, the ratio of diluent and use composition premixed 206 can be adjusted to correspond to different concentration ranges. Thus, a single analytical system can efficiently monitor multiple use compositions in real time or near real time because it can avoid the need for manual predilution for each use composition monitored.

Returning to FIG. 2, after simultaneously dispensing 206 the fluids and premixing the use composition and diluent, the method includes mixing 210 the one or more reagents with the diluted sample to form a mixed sample. The mixing 210 can be carried out in any suitable manner, including through the use of a static mixer such as one of those described herein. After the fluids are mixed 210, the mixed sample flows to a sensor that analyzes the mixed sample to obtain 212 response data. According to some embodiments, the method 200 further includes temporarily stopping the flow of the mixed sample within an optical cell of an optical sensor. In the case of an optical detector, the response data is the measured change in the optical response of the detector over time. In one embodiment, a sensor measures response data by measuring the color change (e.g., absorbance or transmittance) of the mixed sample as a function of time. The response data is indicative of the concentrations of peracid and hydrogen peroxide in the use composition. The concentration of peracid and/or peroxide within the sample is then determined 214 based on the response data. For example, the concentration(s) can be determined according to the peracid/peroxide chemical analysis described in detail in commonly owned U.S. patent application Ser. Nos. 11/810,417 and 12/370,369, or using other analyses known in the art.

According to some embodiments, after collecting the response data, the analytical system may be rinsed and readied for the next monitoring interval. This may occur either simultaneously with or after the concentrations of peracid and peroxide in the use composition are determined. For example, a line connecting the system to the source of use composition may be flushed with the use composition shortly or immediately prior to preparation of the sample mixture to ensure that the measurements are taken using the freshest use composition and thus help to ensure results that they accurately reflect the current concentrations of peracid and/or peroxide in the use composition.

In some embodiments of the invention, the method 200 further includes preparing a reagent blank including only the diluent and one or more reagents without the use composition. The reagent blank allows the system to compensate for any variations in the reagent or the diluent, such as variations in color or other variations, which might affect the transmittance/absorbance of the sample mixture and thus the resulting response of the detector. The response of the detector measured using the reagent blank may then be used as a reference point during calculation of the absorbance of the sample mixture.

In addition to determining the concentrations of one or more substances within a use composition, some embodiments of the invention may also provide for adjusting the concentrations if desired. For example, in systems using the peracid/peroxide chemistry noted above, some methods of the invention further include adding a peracid concentrate composition to a use composition vessel when the peracid concentration is determined to be below a minimum peracid threshold concentration. Some embodiments also provide for emptying the use composition vessel and generating a new use composition when the peroxide concentration is determined to be above a maximum peroxide threshold concentration. As discussed with respect to FIG. 1, in some cases the controller 126 in the analytical system 100 initiates the modification of the use composition, while in other cases, the controller may signal a separate use composition control system.

Figure 3:
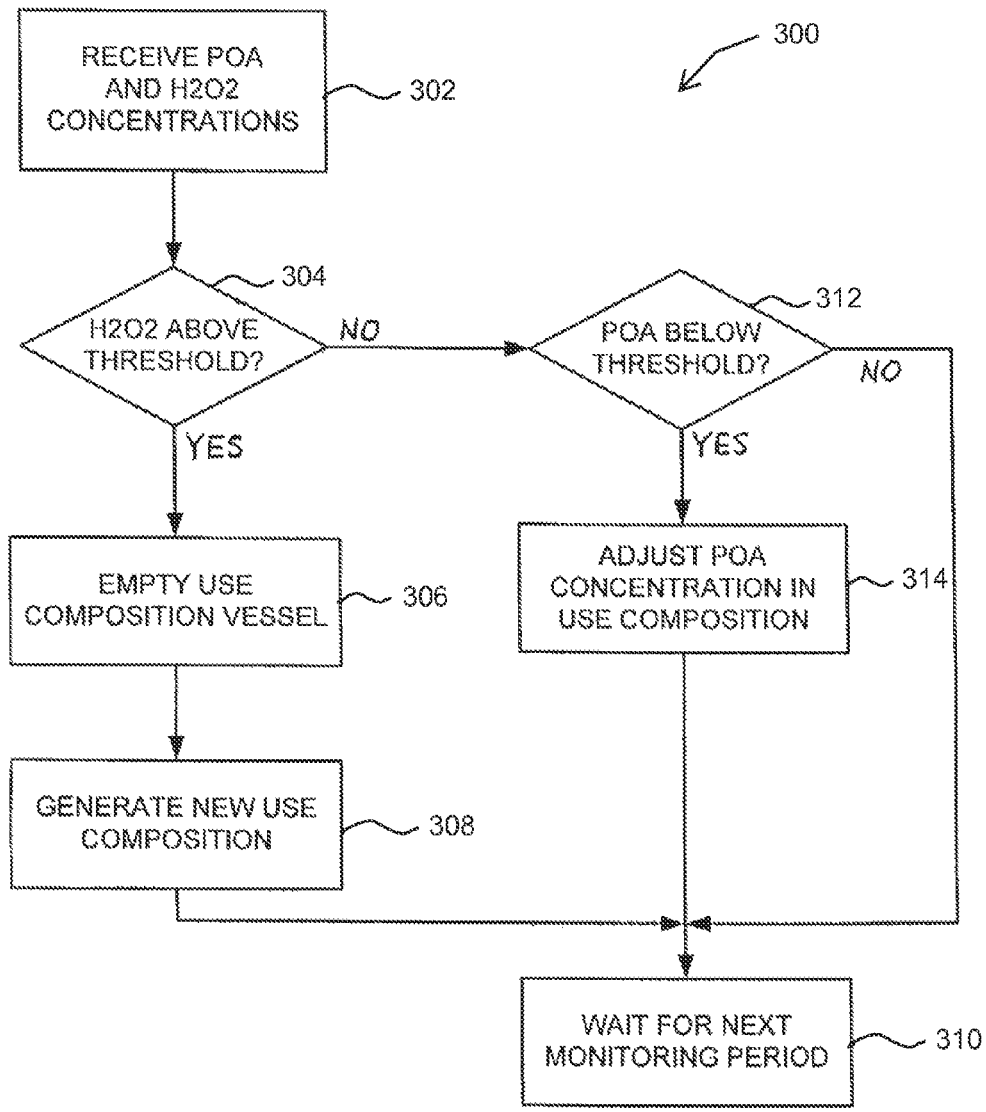
FIG. 3 is a flow diagram illustrating a method of controlling chemical concentrations within a use composition according to some embodiments of the invention.

FIG. 3 is a flow diagram illustrating a method 300 of controlling chemical concentrations within a use composition in certain embodiments of the invention. The method includes determining and/or receiving 302 the peracid and/or peroxide concentrations. The received hydrogen peroxide concentration is compared 304 with a peroxide threshold concentration. If the measured peroxide concentration exceeds the peroxide threshold concentration, a use composition vessel is emptied 306 of the spent use composition. A flow of peracid and diluent into the use composition vessel is then initiated and controller to generate 308 a new use composition. The method 300 then includes waiting 310 for the next monitoring interval, at which point the most recent concentrations of peracid and/or peroxide from use composition monitor are determined/received.

In some cases if the hydrogen peroxide concentration does not exceed the peroxide threshold concentration, the peracid concentration in the use composition is compared 312 with a peracid threshold concentration. If the peracid concentration in the use composition is below the peracid threshold concentration, the peracid concentration in the use composition may be adjusted 314 until it satisfies the peracid threshold concentration. For example, with respect to FIG. 1, the controller 126 may control valves on a peracid concentrate holding tank and/or a diluent holding tank (not shown) such that a given amount of peracid and/or diluent is added to the use composition in use composition vessel (not shown), causing a resultant increase in the concentration of peracid in the use composition.

Figure 4:
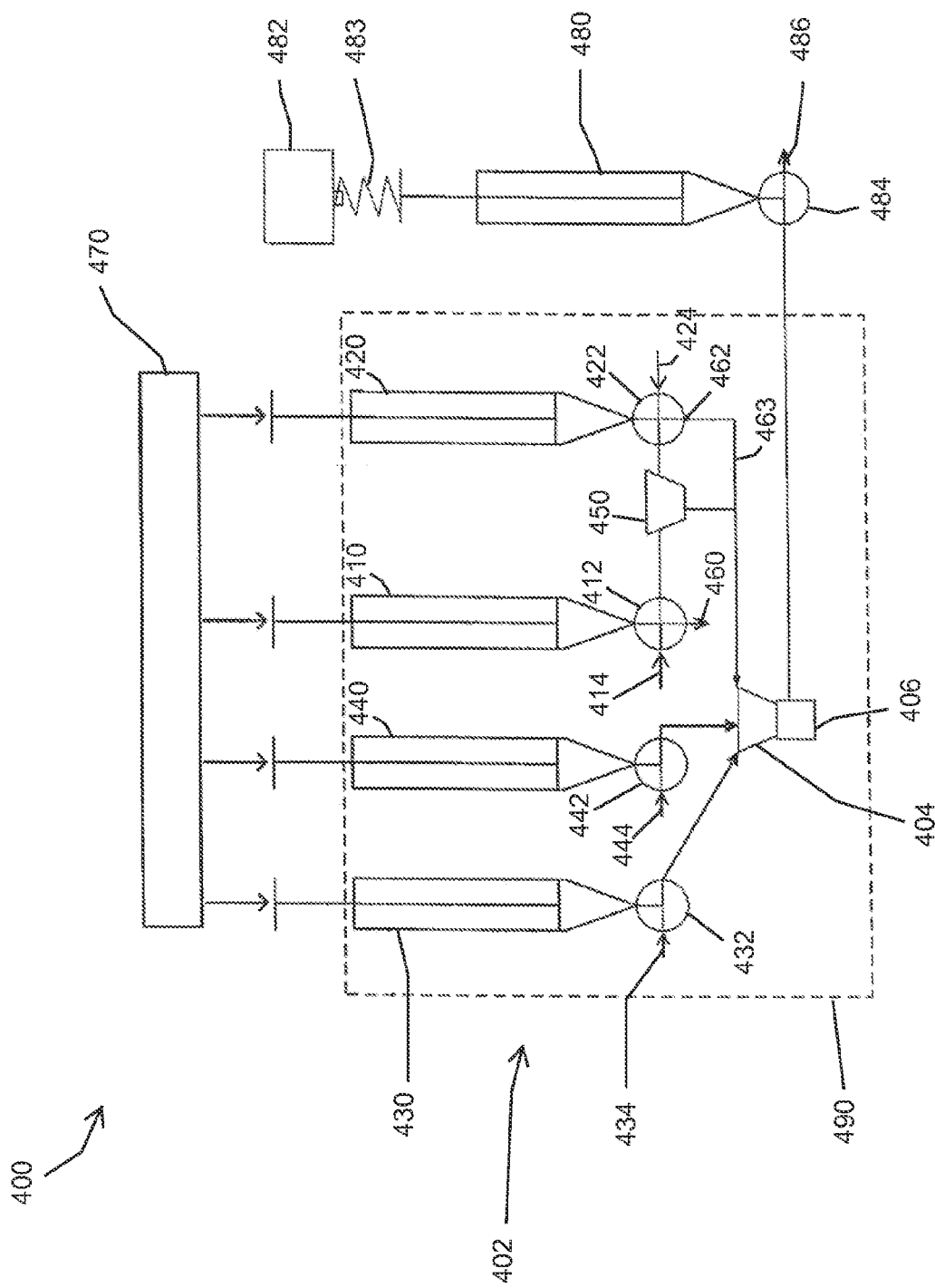
FIG. 4 is a schematic diagram of an analytical system according to some embodiments of the invention.

FIG. 4 is a schematic diagram of an analytical system 400 according to some embodiments of the invention. The system 400 generally includes a sample preparation and dispensing assembly 402 coupled to a mixer 404 and optical sensor 406. Referring to FIG. 1, in some cases the analytical system 400 provides similar functionality to the sample preparation and dispensing assembly 110, the mixer 120 and the sensor 122. Returning to FIG. 4, the analytical system 400 can be used to mix and analyze any desired fluids and/or chemicals. In addition, although the system 400 is depicted with a particular physical embodiment, it should be appreciated that aspects of the system 400 (e.g., number/type of pumps, type of mixer, type of sensor, etc.) can be adapted for dispensing, mixing, and analyzing metered volumes of a wide variety of fluids. For example, while the system depicted in FIG. 4 includes four syringe pumps, it is contemplated that analytical systems may include two or three pumps, or five or more pumps depending upon the needs of a particular chemical analysis being implemented.

In certain embodiments the analytical system 400 is adapted for dispensing, mixing, and analyzing fluids, including a use composition and reagents, according to the peracid/peroxide chemistry described in commonly owned U.S. patent application Ser. Nos. 11/810,417 and 12/370,369. Referring to FIG. 4, the dispensing assembly 402 includes a plurality of syringe pumps (e.g., in this case four) which are coupled through multi-position valves to input ports for ultimately coupling to sources of one or more fluids. For example, the dispensing assembly 402 includes a sample pump 410 coupled to a sample valve 412 that selectively couples the sample pump with a sample input port 414. The sample input port 414 is adapted to couple to a working source of use composition (see, e.g., source 114 in FIG. 1) having concentrations of one or more substances. For example, the use composition may have concentrations of peracid and/or peroxide.

The dispensing assembly 402 also includes a diluent pump 420 coupled to a diluent valve 422 that selectively couples the diluent pump with a diluent input port 424. The diluent input port 424 is adapted to couple to a source of diluent such as water (see, e.g., source 116 in FIG. 1). In addition, the dispensing assembly 402 also includes first and second reagent pump 430, 440 coupled to respective first and second reagent valves 432, 442. The reagent valves selectively couple the first and second reagent pumps 430, 440 with first and second reagent input ports 434, 444, respectively. The first and second reagent input ports are adapted to couple the pumps to sources of a first reagent and a second reagent (see, e.g., sources 112a, 112b in FIG. 1). In some cases the first reagent is an iodide solution with a pH adjusted to an alkaline range, such as potassium iodide. In certain embodiments the second reagent is an acid or an acidic buffer, such as acetic acid.

As shown in FIG. 4, each selector valve also ultimately couples its respective pump to the mixer 404, which is coupled with the optical sensor 406. In some cases, the selector valves may couple the pumps directly to the mixer 404, while in certain cases the selector valves can couple the pumps directly with an intermediate mixing stage before ultimately coupling to the mixer 404. For example, in the embodiment shown in FIG. 4, the first and second pumps 430, 440 are coupled directly to the mixer 404 through the first and second reagent valves 432, 442, respectively. In this case, the sample pump 410 and the diluent pump 420 are directly coupled through the sample and diluent valves 412, 422, respectively, to a premixer 450, and then ultimately coupled to the mixer 404.

In some cases one or more pumps may also be coupled with other inlets and/or outlets, though, e.g., respective selector valves. For example, in the analytical system 400, the sample valve 412 also selectively couples the sample pump 410 to a waste outlet 460 that can be used, for example, to flush the sample pump and/or the sample line connecting the sample pump to the source of use composition. In some cases the diluent pump 420 may also be directly coupled with the mixer 404 in the case that the diluent valve 422 selects a rinse outlet 462. Thus, the diluent pump can be coupled directly to the mixer 404 through a rinse bypass line 463 for, e.g., rinsing the mixer and sensor, or dispensing a reagent blank into the mixer and sensor.

According to some embodiments, the dispensing assembly 402 also includes a driving mechanism 470 that actuates one or more of the syringe pumps. In some cases the driving mechanism 470 includes an independent actuator (e.g., linear driver) coupled to the plunger of each syringe pump, allowing independent control of each pump. For example, captive and non-captive stepper motor linear actuators are available from Haydon Kerk Motion Solutions, Waterbury, Conn. In some cases the driving mechanism 470 includes a single actuator, adapted to drive two or more of the pumps simultaneously. In some cases the single actuator can drive all of the pumps simultaneously. For example, syringe pumps available from New Era Pump Systems, Inc., Wantagh, N.Y., allow for synchronized driving of multiple pumps. As will be described further herein, in certain embodiments a single actuator is provided to simultaneously drive the pumps at two or more different rates. An example of such an "asynchronous" actuator is discussed in further detail with respect to FIGS. 6 and 7. In some cases the path lengths between the pumps and the premixer 450 and the mixer 404 can be optimized depending upon the dispensing rate so that some or all of the dispensed fluids arrive in the mixer at about the same time.

In certain embodiments of the invention, the analytical system 400 is provided in the form of a stop-flow analyzer. The basic form of stop-flow mechanisms are well known. In some cases for example, the system 400 includes a stop syringe 480 in fluid communication with the optical sensor 406. As the driving mechanism 470 dispenses fluids from the pumps, through the mixer 404, and into the sensor 406, the mixed fluids also flow into the stop syringe, triggering a limit switch 482 upon filling the stop syringe 480. Actuating the limit switch can signal the system to stop dispensing the fluids and measure one or more properties of the mixed fluids that are temporarily stopped within the sensor 406. After gathering the desired response data from the sensor 406, a stop valve 484 can select a waste outlet 486 and a spring 483 or other such mechanism can actuate the plunger of the stop syringe 480 to empty the syringe's contents through the waste outlet 486. In some cases the system 400 may then rinse the mixer, sensor, and system lines to ready the system for a next measurement.

Some embodiments of the analytical system 400 are optimized for use as an onsite use composition monitor. While there is a need for accurate and reliable sensors to measure use composition properties onsite, e.g. peracid and peroxide concentrations, local ambient temperature can vary within a wide range. Unstable temperatures inside of the analytical system 400 can in some cases contribute to random variations in concentration readings. Potential causes of such temperature instability include environmental temperature variances and locally generated heat and air flow from components of the measurement system such as pumps, step motors, and electronic components, such as, the controller. Thus, some embodiments provide temperature control (e.g., within a temperature-controlled region 490) through additional features to adjust the temperature of the fluid mixture within the sensor or prior to reaching the sensor. In addition, systems according to some embodiments provide means for adjusting or stabilizing the temperature of sample prior to delivery to the sensor to avoid the inconsistencies associated with in the field operation. Such systems may include those described in commonly owned U.S. patent application Ser. No. 12/370,369, which is incorporated by reference herein.

According to some embodiments of the invention, the first and second reagent pumps 430, 440, the sample pump 410, and the diluent pump 420 are preferably computer controllable bi-directional pumps capable of measuring small volumes (as low as 5-10 µL, for example) with high precision. An example of a suitable syringe pump is the MicroCSP-3000 available from FIAlab Instruments, Bellevue, Wash. An example of other suitable pumps are the M6 or M50 syringe-free pumps available from VICI Valco Instruments Co. Inc., Houston, Tex. However, it should be understood that any suitable pump may be used without departing from the scope of the present invention, and that the invention is not limited in this respect.

In some cases the multi-port reagent, sample, diluent, and stop valves may be implemented using a computer-controlled valve that allows selection of one or more pump/port combinations to intake/receive (aspirate) or expel (dispense) samples, reagents or diluent as necessary in a particular application. Suitable multi-port valves include Cheminert valve Model C25-3184, C25-3186, C25-3188 or C25-3180 multi-port valves with 4, 6, 8 and 10 positions, respectively, available from VICI Valco Instruments Co. Inc., Houston, Tex. Another example of a suitable valve is the M-470 6-Way Medium Pressure Selection Valve available from Upchurch Scientific, Oak Harbor, Wash. In certain embodiments the dispensed fluids move through the system and into the premixer 450, mixer 404, sensor 406, and stop syringe 480 via appropriate tubing. The tubing may be narrow bore plastic tubing with, for example, an inside diameter (ID) of 0.5 mm to 2 mm.

According to some embodiments the mixer 404 can be implemented using any of the schemes described with respect to FIG. 1, such as a static mixer including a piece of tubing with internal baffles that cause flow reversal of the fluids to result in rapid mixing, or any other disclosed or known mixer arrangement. In certain embodiments the premixer 450 is identical to the mixer 404 or incorporates similar technology. For example, the premixer 450 can be a piece of tubing with internal baffles that cause flow reversal of the fluids to result in rapid mixing. The premixer 450 may also be implemented using a knotted reactor, reaction coil, an open tubular reactor, serpentine or other fluid mixing device known in the art. In some cases the premixer 450 may be a laminar flow mixer. An example baffle-type static mixer is the Series 120 Individual Mixing Elements available from TAH Industries Inc, Robbinsville, N.J. In some embodiments, the premixer 450 may take the form of a dynamic mixer such as a jet flow mixer. However, it shall be understood that any suitable mixer may be used without departing from the scope of the present invention, and that the invention is not limited in this respect.

As discussed before, in some cases an analytical system includes an integrated controller or processor that controls the system protocol resulting in aspiration of the sample, reagent (s) and diluent and their transport to sensor 406 for analysis. Software running on the controller can also analyze response data received from sensor 406 and determine the concentrations of peracid and peroxide in the use composition based on the response data. For example, referring to the embodiment in FIG. 1, the controller 126 communicates with the sensor 122 and the sample preparation/dispensing assembly 110 to control operation of the system. Returning to FIG. 4, although not shown, the analytical system 400 can in some cases also include an integral controller in communication with the driving mechanism 470, each of the selector valves, the optical sensor 406, and the limit switch 482 for the stop syringe 480. In addition, such a controller may also communicate with a use composition control system to adjust the concentration of one or more substances within the use composition and/or dump the existing composition and generate a new batch of use composition. Thus in some cases such a controller can coordinate and initiate each measuring cycle and initiate corresponding changes to the use composition if desired.

An example of a measurement cycle according to one embodiment of the invention is shown below:

Sample Sequence
1. Actuate sample valve 412 to direct sample pump 410 to waste outlet 460; actuate pump to flush sample line;
2. Actuate first and second reagent valves 432, 442 to select sources of first and second reagent; actuate sample valve 412 to select source of use composition; actuate diluent valve 422 to select source of diluent;
3. Actuate pumps to aspirate/receive reagents, sample of use composition, and diluent in respective pumps;
4. Actuate first and second reagent valves 432, 442 to select mixer 404; actuate sample valve 412 and diluent valve 422 to select premixer 450;
5. Actuate reagent pumps 430, 440 to drive metered volumes of reagents through mixer 404 into sensor cell 406; actuate sample and diluent pumps 410, 420 to drive metered volumes of use composition and diluent through premixer 450 (forming diluted sample) and mixer 404 (mixing with reagents to form mixed sample) into sensor cell 406;
6. Continue actuating pumps to drive fluids through sensor cell 406 and into stop syringe 480 against force of spring 483; actuate limit switch 482 upon filling stop syringe 480 to start measurement of mixed sample within sensor 406;
7. Measure response data including absorbance vs. time with sensor 406;
8. Actuate stop valve 484 to select waste output 486; actuate stop syringe with spring 483 to discharge waste; actuate stop valve 484 to reselect stop syringe; and
9. Await next measurement cycle.

In some cases the particular reagents, volumes, and dispensing rates can be selected to perform a version of the peracid/peroxide chemical analysis described in detail in commonly owned U.S. patent application Ser. Nos. 11/810, 417 and 12/370,369, the contents both of which are incorporated herein by reference. In addition, the driving mechanism 470 preferably actuates the first and second reagent pumps 430, 440, the sample pump 410, and the diluent pump 420 simultaneously to maximize dispensing and mixing efficiency while minimizing the required time. However, it is also contemplated that in some cases the driving of the pumps may be separated into two or more stages if desired.

The driving mechanism 470 is also preferably adapted to simultaneously drive at least two pumps at different rates. As one example, the driving mechanism may simultaneously drive the diluent pump at a rate that is eight (8) times faster than the sample pump in order to provide a diluted sample having an 8:1 diluent-sample ratio. At the same time, the driving mechanism 470 may drive the first and second reagent pumps at equal rates such that the diluent is dispensed at a rate that is two (2) times faster than the reagents. This case is summarized in Table 1:

TABLE 1

Sample Dispensing Rates

|  | Dispensing Rate (e.g., in µL/sec) | Portion of Mixed Sample |
|---|---|---|
| Sample | X | 1/17 |
| Diluent | 8X | 8/17 |
| First Reagent | 4X | 4/17 |
| Second Reagent | 4X | 4/17 |

Thus, some embodiments of the invention can advantageously provide mixtures of constituent fluids in desired proportions, while also simultaneously dispensing and mixing the fluids to allow for faster measurement cycles. Of course the dispensing rates for each pump will vary depending upon a variety of factors, including the nature of the chemical analysis being performed. For example, in some cases a relatively low concentration of peracid/peroxide within a use composition may be able to be mixed with one or more reagents with only a small amount of additional dilution. In addition, in some cases the pumps preferably have similar or identical characteristics (e.g., volume, nozzle size, plunger length, etc.), although one or more characteristics can be changed in order to introduce another aspect of variability into the system.

Figure 5:
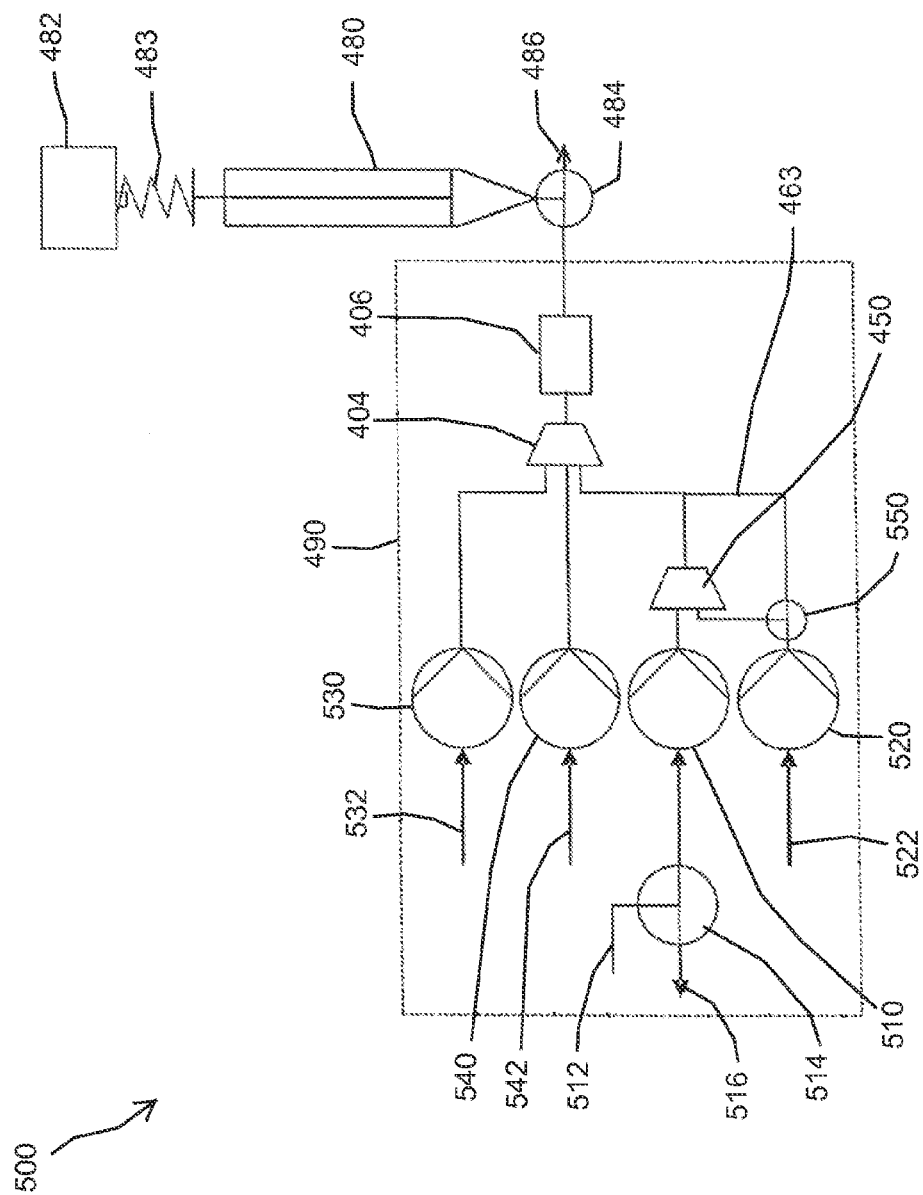
FIG. 5 is a schematic diagram of an analytical system according to some embodiments of the invention.

It should be appreciated that a variety of types of pumps can be utilized in systems according to different embodiments of the invention. FIG. 5 is a schematic diagram of an analytical system 500 utilizing a number of micropumps according to some embodiments of the invention. In addition to the micropumps, the analytical system 500 includes a number of components in common with the analytical system 400 shown in FIG. 4, which are referred to with like numerals. The use of an individual micropump for each fluid provides another manner in which independent control can be provided for each fluid, enabling simultaneous fluid dispensing in addition to different dispensing rates if desired. In addition, the use of micropumps can provide advantages over the use of syringe pumps, such as compact size, simplified control, and internal valving, thus reducing the need for independent, computer-controlled selector valves. Any suitable micropump known in the art can be utilized, and the scope of the invention is not limited in this respect. For example, the micropumps can include syringe pumps of varying sizes, peristaltic, pneumatic or diaphragm pumps, gear pumps, oval gear pumps, among other types of pumps. In some cases embodiments of the invention may incorporate one or more of the pumps described in commonly owned U.S. patent application Ser. Nos. 12/474,474 and 12/565,520, the contents both of which are hereby incorporated by reference in their respective entireties.

Referring again to FIG. 5, the analytical system 500 includes a sample pump 510, a diluent pump 520, a first reagent pump 530, and a second reagent pump 540. Each pump is coupled to a respective input port (sample input port 512, diluent input port 522, first reagent input port 532, second reagent input port 542) and also ultimately coupled to the mixer 404 and sensor 406. According to some embodiments, a sample valve 514 selectively couples the sample pump 510 with the sample input port 512 and a waste outlet 516, which can allow flushing of the sample line if desired. In some cases a premixer 450 is also coupled between the sample and diluent pumps 510, 520 and the mixer 404, to allow for predilution of the sample as describe above. In addition, a diluent valve 550 can selectively couple the diluent pump with the premixer 450 or in some cases a rinse bypass line 463 to enable rinsing of the mixer and sensor.

Figure 6:
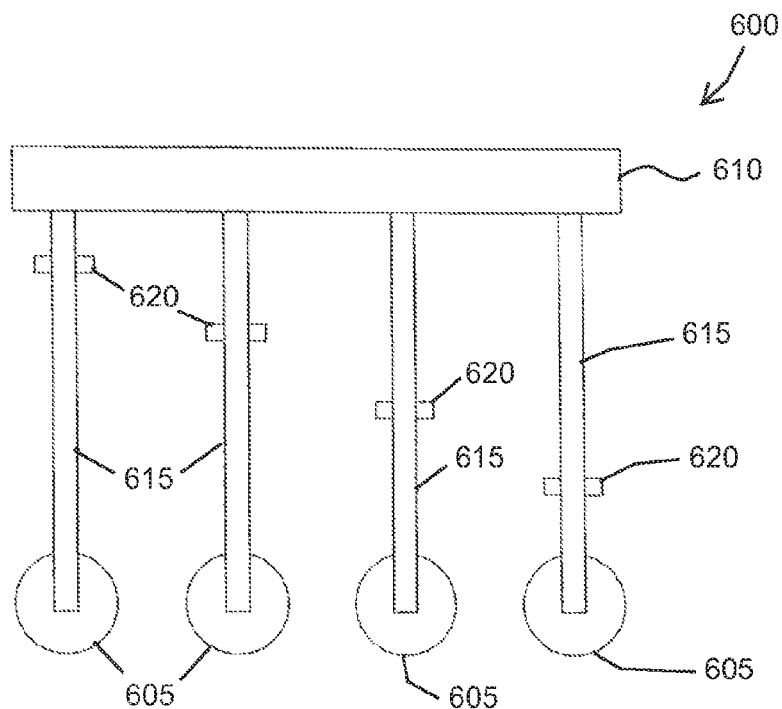
FIG. 6 is schematic top view of an actuator and a number of syringe pumps according to some embodiments of the invention.
Figure 7:
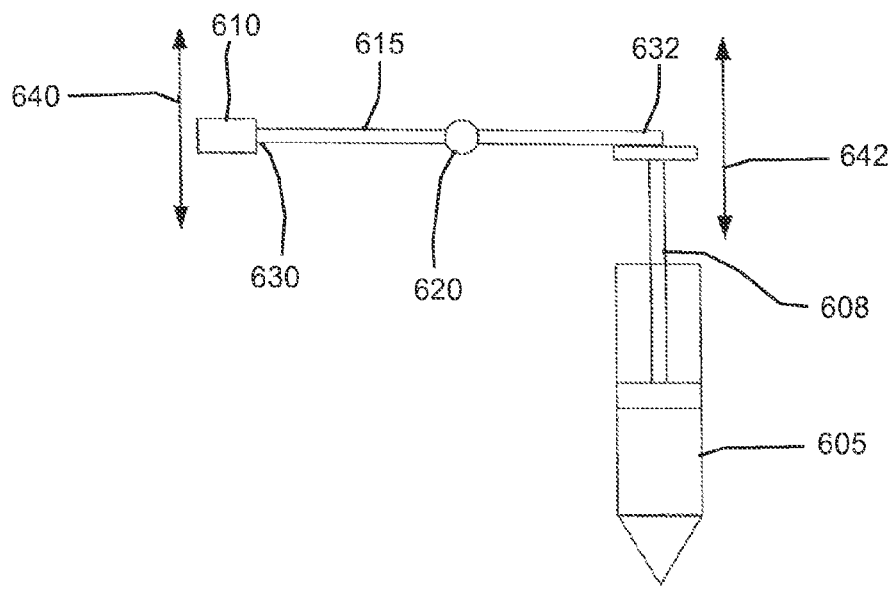
FIG. 7 is a schematic side view of an actuator and syringe pump according to some embodiments of the invention.

As discussed above, in certain embodiments of the invention fluids may be dispensed at different rates to provide mixtures of fluids in different proportions. FIGS. 6 and 7 illustrate an example of an asynchronous or asymmetric actuator 600 including multiple syringe pumps 605 that are driven at different rates by a single driving mechanism 610. FIG. 6 is a schematic top view of the asynchronous actuator 600 and the syringe pumps 605, while FIG. 7 is a schematic side view of the asynchronous actuator 600 and a single syringe pump 605 according to some embodiments of the invention.

As shown in FIGS. 6 and 7, the asynchronous actuator 600 is adapted to simultaneously drive multiple syringe pumps 605 by actuating a single driving mechanism 610 that in turn actuates individual force levers 615 coupled to respective pumps 605. According to some embodiments, a pivot 620 is placed at a desired location along each force lever 615 to enable the force levers to actuate the syringe pumps 605 at varying rates according to the position of each respective pivot 620. For example, FIG. 7 shows a single force lever 615 coupled at a first end 630 to the driving mechanism 610, and at a second end 632 to the syringe plunger 608. In a preferred embodiment each force lever 615 is coupled to the driving mechanism 610 through an articulating connection mechanism (not shown in FIGS. 6 and 7), such that each force lever 615 is able to move independently (e.g., at different rates) from other force levers as the driving mechanism 610 is moved up and down through a driving distance 640. As the driving mechanism 610 moves through the driving distance 640, the force lever 615 rotates about the pivot 620, thus moving the second end 632 of the lever and the syringe plunger 608 through a plunger distance 642. In a preferred embodiment, the second end 632 of each force lever 615 is movably coupled (e.g., in sliding engagement) to a respective syringe plunger 608 (not shown in FIGS. 6 and 7), and so is capable of pushing the plunger 608 down and pulling the plunger 608 up through the plunger distance 642 based on movement of the driving mechanism 610. The ratio of the driving distance 640 to the plunger distance 642 can be adjusted by moving the pivot 620 along the lever.

Accordingly, by driving the first end 630 of each force lever the same driving distance 640, the driving mechanism 610 drives the second end 632 of each force lever, along the coupled syringe plunger, through potentially different plunger distances. Thus, in some cases the driving mechanism can simultaneously drive the first ends of the levers at a constant rate, which produces simultaneous plunger movement at different rates depending upon the position of the pivot 620 with respect to each force lever 615.

Figure 8:
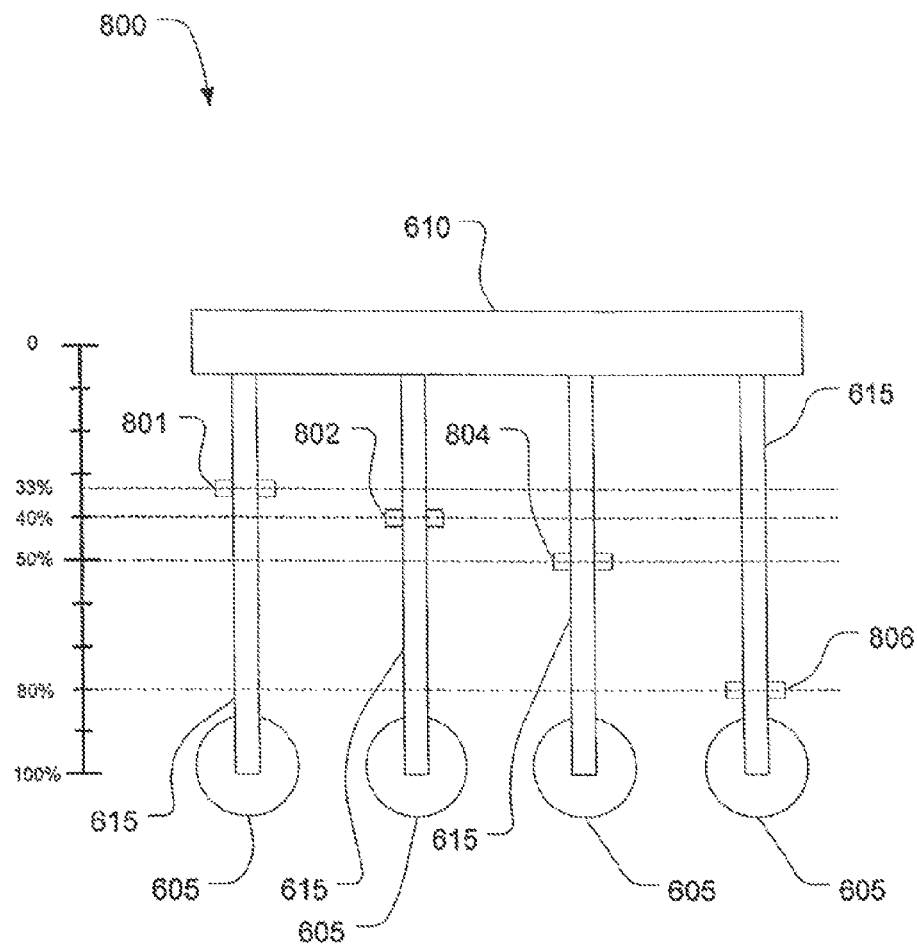
FIG. 8 is a graphical depiction of different pivot positions along multiple force levers according to an embodiment of the invention.

FIG. 8 is a schematic top view of an asynchronous actuator 800 including multiple force levers 615 and syringe pumps 605, and a graphical representation of the pivot placement for each force lever according to an embodiment of the invention. As shown in FIG. 8, the pivots 801, 802, 804, and 806 are each located at a different position between the first and second ends of the force levers. The relative positions of the pivots can be set to adjust the distance that each plunger travels during movement of the driving mechanism 610. For example, as the driving mechanism 610 raises the first ends of the force levers 615, the second ends of the force levers push each syringe plunger down a distance corresponding to the placement of the pivot for each particular force lever. In some embodiments the driving mechanism 610 actuates all the force levers simultaneously, thus causing each syringe plunger to simultaneously travel through its entire distance during the same time period, leading to different dispensing rates. Table 2 below provides an example of relative movement and dispensing rates corresponding to different pivot locations according to some embodiments of the invention. Of course, a wide variety of pivot positions are possible, depending upon the desired plunger travel and dispensing rate for a particular syringe pump.

TABLE 2

Relative Plunger Movement

| Pivot | 801 | 802 | 804 | 806 |
|---|---|---|---|---|
| Relative Position | 33% | 40% | 50% | 80% |
| Relative Driving Distance | 0.19537 | 0.19537 | 0.19537 | 0.19537 |
| Relative Plunger Distance | −0.39079 | −0.293048 | −0.195366 | −0.048841 |
| Relative Dispensing Rate | 2.00 | 1.50 | 1.00 | 0.25 |

Use compositions including peracids and peroxides described herein may be used for a variety of domestic or industrial applications, e.g., to reduce microbial or viral populations on a surface or object or in a body or stream of water. The compositions may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or nonwoven fabric, soft plastics and elastomers. The compositions may also be applied to soft surfaces such as food and skin (e.g., a hand). The use compositions may be employed as a foaming or nonfoaming environmental sanitizer or disinfectant.

The compositions may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions may also be used in veterinary products such as mammalian skin treatments or in products for sanitizing or disinfecting animal enclosures, pens, watering stations, and veterinary treatment areas such as inspection tables and operation rooms. The compositions may be employed in an antimicrobial foot bath for livestock or people.

The compositions may be employed for reducing the population of pathogenic microorganisms, such as pathogens of humans, animals, and the like. The compositions may exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The compositions may reduce the population of microorganisms on skin or other external or mucosal surfaces of an animal. In addition, the compositions may kill pathogenic microorganisms that spread through transfer by water, air, or a surface substrate. The composition need only be applied to the skin, other external or mucosal surfaces of an animal water, air, or surface.

The compositions may also be used on foods and plant species to reduce surface microbial populations; used at manufacturing or processing sites handling such foods and plant species; or used to treat process waters around such sites. For example, the compositions may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions may be used to treat produce transport waters such as those found in flumes, pipe transports, cutters, slicers, blanchers, retort systems, washers, and the like. Particular foodstuffs that may be treated with compositions include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The composition may be useful in the cleaning or sanitizing of containers, processing facilities, or equipment in the food service or food processing industries. The compositions may be used on food packaging materials and equipment, including for cold or hot aseptic packaging. Examples of process facilities in which the compositions may be employed include a milk line dairy, a continuous brewing system, food processing lines such as pumpable food systems and beverage lines, etc. Food service wares may be disinfected with the compositions. For example, the compositions may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions may also be used on or in other industrial equipment and in other industrial process streams such as heaters, cooling towers, boilers, retort waters, rinse waters, aseptic packaging wash waters, and the like. The compositions may be used to treat microbes and odors in recreational waters such as in pools, spas, recreational flumes and water slides, fountains, and the like.

A filter containing a composition may reduce the population of microorganisms in air and liquids. Such a filter may remove water and air-born pathogens such as *Legionella*.

The compositions may be employed for reducing the population of microbes, fruit flies, or other insect larva on a drain or other surface.

The compositions may also be employed by dipping food processing equipment into the use solution, soaking the equipment for a time sufficient to sanitize the equipment, and wiping or draining excess solution off the equipment. The compositions may be further employed by spraying or wiping food processing surfaces with the use solution, keeping the surfaces wet for a time sufficient to sanitize the surfaces, and removing excess solution by wiping, draining vertically, vacuuming, etc.

The compositions may also be used in a method of sanitizing hard surfaces such as institutional type equipment, utensils, dishes, health care equipment or tools, and other hard surfaces. The composition may also be employed in sanitizing clothing items or fabrics which have become contaminated. The composition is contacted with any contaminated surfaces or items at use temperatures in the range of about 4° C. to 60° C., for a period of time effective to sanitize, disinfect, or sterilize the surface or item. For example, the composition may be injected into the wash or rinse water of a laundry machine and contacted with contaminated fabric for a time sufficient to sanitize the fabric. Excess composition may be removed by rinsing or centrifuging the fabric.

The compositions may be applied to microbes or to soiled or cleaned surfaces using a variety of methods. These methods may operate on an object, surface, in a body or stream of water or a gas, or the like, by contacting the object, surface, body, or stream with a composition. Contacting may include any of numerous methods for applying a composition, such as spraying the composition, immersing the object in the composition, foam or gel treating the object with the composition, or a combination thereof.

The composition may be employed for bleaching pulp. The compositions may be employed for waste treatment. Such a composition may include added bleaching agent.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A stop-flow analytical system, comprising:
   a sample pump coupled with a sample input port that allows the sample pump to be coupled to a working source of a use composition having concentrations of one or more substances;
   a first reagent pump coupled with a first reagent input port that allows the first reagent pump to be coupled with a source of a first reagent;
   a diluent pump coupled with a diluent input port that allows the diluent pump to be coupled with a source of a diluent;
   a pre-mixer coupled to the sample pump and the diluent pump, the pre-mixer configured to mix together a finite sample of the use composition delivered by the sample pump and a finite volume of the diluent delivered by the diluent pump, resulting in a diluted sample;
   a mixer coupled to the first reagent pump and the pre-mixer, the mixer configured to mix together a finite volume of the first reagent delivered by the first reagent pump and the diluted sample received from the pre-mixer, resulting in a sample mixture;
   an optical sensor coupled to the mixer, the optical sensor comprising an optical cell that receives the sample mixture from the mixer, the optical sensor configured to obtain response data from the sample mixture indicative of the concentrations of the one or more substances within the use composition;
   a stop-flow mechanism coupled to the optical sensor and configured to stop the flow of the sample mixture while the sample mixture is within the optical cell of the optical sensor; and
   a rinse bypass line coupling the diluent input port to the mixer while bypassing the pre-mixer.

2. The analytical system of claim 1, wherein the pre-mixer is a static mixer.

3. The analytical system of claim 2, wherein the static mixer is a piece of tubing with internal baffles, a knotted reactor, a reaction coil, an open tubular reactor, or a serpentine mixing device.

4. The analytical system of claim 1, wherein the pre-mixer is a laminar flow mixer.

5. The analytical system of claim 1, wherein the rinse bypass line couples the diluent pump directly to the mixer.

6. The analytical system of claim 1, further comprising a second reagent pump coupled with a second reagent input port that allows the second reagent pump to be coupled with a source of a second reagent, wherein the mixer is further coupled to the second reagent pump and configured to mix together a finite volume of the second reagent delivered by the second reagent pump with the volumes of the first reagent and the diluted sample.

7. The analytical system of claim 6, wherein the sample pump is coupled to a working source of a use composition having concentrations of one or more substances, and wherein the one or more substances comprise a peracid and a peroxide.

8. The analytical system of claim 7, wherein
   the first reagent pump is coupled with a source of a first reagent via the first reagent input port;
   the second reagent pump is coupled with a source of a second reagent via the second reagent input port; and
   the first reagent comprises an iodide solution with a pH adjusted to an alkaline range and the second reagent comprises an acid or an acidic buffer.

9. The analytical system of claim 8, wherein the first reagent comprises potassium iodide and the second reagent comprises acetic acid.

10. The analytical system of claim 1, wherein the sample pump, the first reagent pump, and the diluent pump each comprise a micropump.

11. The analytical system of claim 1, wherein the sample pump, the first reagent pump, and the diluent pump each comprise a syringe pump having a plunger.

12. The analytical system of claim 11, further comprising a first reagent valve selectively coupling the first reagent pump with the first reagent input port and the mixer, a sample valve selectively coupling the sample pump with the sample input port and the pre-mixer, and a diluent valve selectively coupling the diluent pump with the diluent input port and the pre-mixer.

13. The analytical system of claim 12, wherein the diluent valve also selectively couples the diluent pump with the rinse bypass line coupled to the mixer.

14. The analytical system of claim 11, further comprising an asynchronous actuator mechanically coupled to each of the plungers of the sample pump, the first reagent pump and the diluent pump and configured to simultaneously drive at least two of the plungers of the sample pump, the first reagent pump, and the diluent pump at different rates.

15. The analytical system of claim 14 wherein the asynchronous actuator comprises a driving mechanism, a sample lever, a first reagent lever, and a diluent lever, the levers coupled at a first end to the driving mechanism and at a second end to the plungers of the sample pump, the first reagent pump, and the diluent pump, respectively, wherein actuation of the driving mechanism simultaneously displaces the first end of each of the levers by a respective driving distance and the second end of each of the plurality of levers by a respective plunger distance.

16. The analytical system of claim 15, wherein the driving distance of each of the levers is the same and the plunger distance of at least two of the levers is different.

17. The analytical system of claim 1, further comprising a processor coupled to the optical sensor, the processor programmed with instructions for determining the concentrations of the one or more substances based on the response data and instructing a use composition controller to modify or replace the use composition based on the determined concentrations of the one or more substances.

18. An analytical system, comprising:
sample pumping means coupled with a sample input port that allows the sample pumping means to be coupled to a working source of a use composition having concentrations of one or more substances;
first reagent pumping means coupled with a first reagent input port that allows the first reagent pumping means to be coupled with a source of a first reagent;
second reagent pumping means coupled with a second reagent input port that allows the second reagent pumping means to be coupled with a source of a second reagent;
diluent pumping means coupled with a diluent input port that allows the diluent pumping means to be coupled with a source of a diluent;
pre-mixing means coupled to the sample pumping means and the diluent pumping means, for mixing together a finite sample of the use composition delivered by the sample pumping means and a finite volume of the diluent delivered by the diluent pumping means, resulting in a diluted sample;
mixing means coupled to the first reagent pumping means, the second reagent pumping means, and the pre-mixing means, for mixing together a finite volume of the first reagent delivered by the first reagent pumping means, a finite volume of the second reagent delivered by the second reagent pumping means, and the diluted sample received from the pre-mixing means, resulting in a sample mixture;
optical sensing means coupled to the mixing means for receiving the sample mixture from the mixing means and obtaining response data from the sample mixture indicative of the concentrations of the one or more substances within the use composition; and
stop-flow means coupled to the optical sensing means for stopping the sample mixture while obtaining the response data from the sample mixture.

19. The analytical system of claim 18, further comprising a rinse bypass line coupling the diluent pumping means directly to the mixing means.

20. The analytical system of claim 18, wherein the one or more substances comprise a peracid and a peroxide.

21. The analytical system of claim 20, wherein the first reagent comprises an iodide solution with a pH adjusted to an alkaline range and the second reagent comprises an acid or an acidic buffer.

22. The analytical system of claim 18, further comprising driving means mechanically coupled to each of the sample pumping means, the first reagent pumping means, the second reagent pumping means, and the diluent pumping means for driving at least two of the sample pumping means, the first reagent pumping means, the second reagent pumping means, and the diluent pumping means at different rates.

23. The analytical system of claim 18, further comprising processing means coupled to the optical sensing means for determining the concentrations of the one or more substances based on the response data and instructing a use composition controller to modify or replace the use composition based on the determined concentrations of the one or more substances.

24. A method for determining concentrations of a peracid and/or a peroxide within a use composition, the method comprising:
receiving with a sample pump a use composition having concentrations of a peracid and/or a peroxide from a working source of the use composition;
receiving with a first reagent pump a first reagent;
receiving with a second reagent pump to a second reagent;
receiving with a diluent pump a diluent;
simultaneously actuating the sample pump, the first reagent pump, the second reagent pump, and the diluent pump to dispense a finite sample of the use composition, a finite volume of the first reagent, a finite volume of the second reagent, and a finite volume of the diluent;
pre-mixing the sample of the use composition and the volume of the diluent to form a diluted sample;
mixing the volumes of the first reagent and the second reagent with the diluted sample to form a mixed sample;
stopping the mixed sample within an optical cell of an optical sensor;
obtaining optical response data from the mixed sample while the mixed sample is stopped within the optical cell of the optical sensor, the response data indicative of the concentrations of the peracid and/or the peroxide; and
determining the concentrations of the peracid and/or peroxide based on the optical response data.

25. The method of claim 24, wherein the first reagent comprises an iodide solution with a pH adjusted to an alkaline range and the second reagent comprises an acid or an acidic buffer.

26. The method of claim 24, further comprising simultaneously actuating the sample pump, the first reagent pump, the second reagent pump, and the diluent pump to simultaneously draw the sample of the use composition, the volume of the first reagent, the volume of the second reagent, and the volume of the diluent from their respective sources.

27. The method of claim 26, further comprising selectively coupling the sample pump to a pre-mixer after drawing the sample of the use composition, selectively coupling the diluent pump to the pre-mixer after drawing the volume of the diluent, selectively coupling the first reagent pump to a mixer after drawing the volume of the first reagent, and selectively coupling the second reagent pump to the mixer after drawing the volume of the second reagent.

28. The method of claim 27, further comprising rinsing the mixer with the diluent.

29. The method of claim 26, further comprising flushing a sample line coupled between the source of the use composition and the sample pump before drawing the sample of the use composition.

30. The method of claim 24, further comprising adding a peracid concentrate composition to the use composition when the peracid concentration is determined to be below a minimum peracid threshold concentration.

31. The method of claim 24, further comprising generating a new use composition when the peroxide concentration is determined to be above a maximum peroxide threshold concentration.

32. The method of claim 24, further comprising dispensing at different rates at least two of the volume of the first reagent, the volume of the second reagent, the sample of the use composition, and the volume of the diluent.

33. The method of claim 32, wherein the first reagent pump, the second reagent pump, the sample pump, and the diluent pump each comprise a syringe pump having a plunger, and further comprising actuating the plungers of at least two of the first reagent pump, the second reagent pump, the sample pump, and the diluent pump at different rates with a single driving mechanism.

34. The method of claim 24, further comprising coupling the sample pump to a working source of the use composition and coupling the diluent pump to a source of the diluent.

\* \* \* \* \*